(12) United States Patent
Jederström

(10) Patent No.: US 6,448,093 B1
(45) Date of Patent: *Sep. 10, 2002

(54) HYDROPHOBE BIOMOLECULAR STRUCTURE

(76) Inventor: Gustaf Jederström, Rörstrandsgatan 22, SE-11340 Stockholm (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/455,472

(22) Filed: Dec. 6, 1999

(30) Foreign Application Priority Data

Nov. 15, 1999 (SE) ................................. 9904121

(51) Int. Cl.$^7$ .................. G01N 33/544; G01N 33/546; C07H 21/04
(52) U.S. Cl. .................. 436/528; 436/534; 536/23.1
(58) Field of Search ................. 436/528, 534; 530/812; 536/23.1

(56) References Cited

U.S. PATENT DOCUMENTS

| | | | |
|---|---|---|---|
| 4,141,973 A | 2/1979 | Balazs | 514/54 |
| 5,654,006 A * | 8/1997 | Fernandez et al. | 424/489 |
| 5,844,107 A * | 12/1998 | Hanson et al. | 536/23.1 |
| 6,087,171 A * | 7/2000 | Neuman et al. | 435/375 |

FOREIGN PATENT DOCUMENTS

| | | | | |
|---|---|---|---|---|
| EP | 014995 A2 | | 3/1980 | |
| EP | 014996 | * | 9/1980 | ................. 514/772 |
| EP | 0 522 491 | | 1/1993 | |
| JP | 10158196 | * | 6/1998 | ................. 514/772 |
| WO | 90/05522 | | 5/1990 | |
| WO | 97/15330 | | 5/1997 | |
| WO | WO 97/15330 | * | 5/1997 | ................. 514/769 |

* cited by examiner

Primary Examiner—Terry McKelvey
Assistant Examiner—William Sandals
(74) Attorney, Agent, or Firm—Young & Thompson

(57) ABSTRACT

The present invention relates to a new hydrophobe biomolecular structure, which is compacted due to the passing of the structure over its point of collapse, a method for the preparation of the structure and use of the new structure for the manufacture of a medicament.

7 Claims, 10 Drawing Sheets

Protonbinding of deprotonized/protonized rhGH in the intervals 10,4-3,8 and 4,2-9,9 determined after acid-base titration of $1,3*10^{-1}$ M rhGH in 0,1 M KCl. Protonbinding is given in Mol H+ ions per Mol rhGH at different pH. Corresponding blanks are subtracted.

HYDROPHOBE BIOMOLECULAR STRUCTURE

The present invention relates to a new hydrophobe biomolecular structure, a method for the preparation of the structure and use of the new structure for the manufacture of a medicament.

BACKGROUND

When a cell should be intro-transfected with DNA and/or a plasmid the molecule should not be bigger than 10 nm and have hydrophobic properties. It also must be stable enough so that the plasmid/DNA can be handled.

The administration of a peptide to a patient is normally performed by injection, as biological uptake of a peptide by other routes of administration is difficult. The molecule to be introduced should not larger than 10 nm and have hydrophobic properties.

Hyaluronic acid (Hy) is a naturally occurring glycosaminoglycan consisting of a linear polymer of repeating units of glucuronic acid and N-acetyl-glucosamine. The molecular weight can vary over a wide range depending on the source. Hy is present in several tissues of animals, and in some organs, such as rooster combs, in concentrations high enough for commercial scale extraction. Such tissue contains Hy of a wide range of molecular weights and during a complex series of extraction, purification and sterilisation steps, high molecular weight chains are more or less degraded resulting in a final product having a considerably narrower molecular weight range.

Hy is non-toxic and is decomposed in the body and thus suitable for pharmacological use.

A commercial available hyaluronic acid product is HEALON® (Kabi Pharmacia AB, Uppsala, Sweden) which has a average molecular weight of about 4000000 Dalton. This product is produced as outlined in U.S. Pat. No. 4,141,973 and is an ultra-pure product. There are many literature references relating to the use of viscoelastic products of HA in ophthalmologic application and the preparation of such products, including the preparation of chemically modified HA.

Hy is known in slow release formulations and in WO 9005522 HA is mentioned as a slow release carrier together with a binding protein for e.g. CH or IGF.

Low molecular weight hyaluronic acid LMWHA is known as carrier for pharmaceutical active agents and for pharmaceutical activity by itself.

EP 522 491 discloses a freeze-dried composition comprising hyaluronic acid arid a polypeptide, which is administered by injection after reconstitution of the composition.

A patent application, WO 97/15330, claiming Hyaluronic acid as DNA carrier for gene Therapy and VEGF antisense DNA to treat abnormal retinal vascularisation was published May 1, 1997.

Hyaluronic acid molecular mass 300–5000 kDalton is claimed to increase viral vectors uptake by adjuvant effect page 33.

The mechanisms is suggested to be of targeting nature, that is, Hy binds to the cell receptor and to an adeno-virus construct increasing the contact time which facilitate and increase the efficiency of transfection page 55.

The goal of the compaction of biomolcules is to improve the oral bioavailability of peptides and thereby avoid the need of parental administration.

The used procedure will also improve the transfection efficiency of genes into mammalian cells for a stable expression and thereby avoid the need of toxic plasmid-DNA complex resulting in a short living expression and in side effects.

Full biological effect of compact peptide is demonstrated in biological assay and in vivo. The size and the durable hydrophobic properties obtained at pH 6 of the peptide suggest an improved oral bioavailability. Plasmid-DNA complex has been compact from 87 nm to 7.5 nm suggesting an improved transfection efficiency of genes.

Peptides are compacted from 2.4 nm to <0.3 nm, improving its ability to penetrate across biological membranes e.g. the gut wall and the stratum corneum. The plasmid-DNA construct is compacted from 87 nm to <10 nm, improving the DNA-structure for free passage through the nuclear pore. These new hydrophobic structures are obtained by pH-shifts, by elimination of molecular charge and bindings, by evacuation of water and ions, and finally stabilised with Hyaluronan.

These compacted structures can be administrated by new routes and thereby avoid the need of parental administration. Examples of these structures are peptides such as growth factors, metabolic regulators such as insulin and the like, plasmid-DNA and related bio-active molecules such as naked DNA, RNA and poly-electrolyte structures such us heparin and heparin derivatives. The routes include oral-, pulmonary-, nasal-, topical administration and intra cellular trafficking. These routes will make drug application more convenient especially for children. The drug will also be easier to handle which will result in an improved compliance. The cost of production for most of these drugs will be less since there are no requirements for sterile production of drugs administered the suggested way.

Pharmaceutical research is today devoted to improve the ability of the drug to penetrate biological membrane. One approach is to entrap bio-molecules in carrier system such as bioadhesive gels, liposomes or micro-beads.

Another approach is to replace peptides and related biological molecules with organic compounds designed for oral delivery and with a molar mass less than 500 Dalton. These structures are screened for activation of soluble receptors in tracks with around 96 probes. In about 75000 structures can easily be evaluated in a short time. Up til now however no active structure has been found although the screening started for around 10 years ago.

Compacting of well-known peptides such as growth hormones and insulin as well as uncomplicated DNA structures will eliminate expansive and extended toxicological studies. Clinical studies of these compacted structures will also be less complicated than for those studies required for new chemical entities and for entrapped bio-structures in liposome, micro-spheres and related carrier systems.

Thus, one embodiment of the present invention is a hydrophobe biomolecular structure containing a polymer and a polar biostructure. The structure is derived from collapsing the structure, when the structure is made to pass over the structure's point of collapse. The result will be a compacted hydrophobic structure with buried polar groups and a minimum size, and the polymer is surrounding the biostructure.

In a prefered embodiment of the inventive hydrophobic biomolecular structure is:

the polymer a glycosaminoglycan such as hyaluronic acid or a cationic polysaccharide such as chitosan; and the polar biostructure a nucleotide such as plasmid-DNA, DNA or RNA, a peptide such as insulin, growth hormone, recombinat growth hormone, heparin, heparin derivatives or enzyme, or a monoclonal.

Another embodiment of the present invention is a method for the production of the hydrophobic biomolecular structure. The method includes the steps of:

a) solubilisation of the polymer and solubilisation of the polar biostructure by addition of an acid;

b) collapsing the polar biostructure by addition of an electrolyte by passing the polar biostructure over polar biostructure's point of collapse and changing the hydrodynamic randii to a minimum compact size; and c) dialysing the biomolecular structure, thereby obtaining a compacted hydrophobic structure with the polar groups buried and the polymer surrounding the biostructure.

In a prefered embodiment of the inventive method the acid in step a) is hydrochloric acid, sulphuric acid, phosphoric acid or acetic acid and the pH is less than 3, preferable in the range of 1.0 to 2.5.

In another prefered embodiment of the inventive method the electrolyte of step b) contains cations such as $NH_4^+$, $K^+$, $Na^+$, $Ca^{2+}$, $Mg^{2+}$, $Zn^{2+}$, $Fe^{2+}$, $Fe^{3+}$ and anions such as sulfates, chloride, acetates.

In another embodiment of the present invention the hydrophobic biomolecular structure is used as a medicament.

Preferred embodiments and other aspects of the present invention are defined in the independent and the dependent claims.

INVENTION

Hy is normally in the form of loops, but to our surprise, we have found that it can become straight in the presence of protons, H+.

Thus, when HCl is added to a solution of Hy, the molecules will become straight and will be positively charged.

By Hy is here meant Hyaluronan with a molecular weight of 150 kDa in a range of 80–360 kDa.

An optimal compaction (=size) and hydrophobic properties of plasmid (<10 nm) and peptides (<0.3 nm) are found by elimination of charge and molecular bindings by addition of HCl to pH<2 and of different ions. These ions are cationic ions: $NH_4^+$, $K^+$, $Na^+$ and anionic ions: sulfates, chloride, carbonates, acetates.

A stable complex/polymer is formed by Hy surrounding the plasmid, the peptides respectively when Hy is changing its structure back to a curling like structure when pH is changed to pH 6. It is then possible to dilute the solutions to the desired strength.

I. Plasmids

Historically transfection of plasmid/DNA into cells has been performed by either using a signal substance or by passive diffusion. A compaction=compression of plasmid, which are about 60 to 500 nm, results in a much smaller molecules. Transfection with small molecules has earlier been performed with the use of lipid-amine-complexes or sodium chloride. However, these amines result in a toxic complex for the cell and are thus not suitable. When NaCl alone is used, the complex is not stable.

The compaction according to our invention occurs when NaCl or $Na_2SO_4$ and HCl are mixed with the plasmid. The water, which was included in the plasmid, is evacuated and hydrogen bridges are eliminated.

The molecules become more negatively charged and more hydrophobic.

When the straightened Hy and the compressed plasmid are mixed at low pH and dialysed to a pH of about 6.5 a stable complex is formed with a diameter of about 7.5 nm.

This complex is stable for at least 3 month in aqueous solution and is non-toxic.

II Peptides

Recombinant growth hormone, rhGH is here used as an example of a peptide of great medical interest.

rhGH has a size of about 2.4 nm and cannot be given orally because of its size, its hydrophobic properties and its ease to be bio-graded. This unable rhGH like most other peptides to pass bio-membranes. When rhGH is in a solution at its isoelectric point the molecule is not charged and is hydrophobic. If straightened Hy is added, complexes are formed in which the rhGH molecule is "surrounded" by Hy and the particles are less than 1 nm. These particles appear stable and could be administered orally.

Method of Compaction

By changing pH to a strong acid solution (pH 1.5) peptides gets easily soluble and Hy becomes a charged structure stretching out from a curling cylinder to straight line. By adding electrolytes to the solution a minimum of charge occurs in the peptide. This results in a total collapse of the peptide structure as it passes its pI (isoelectric point).In regulating the ions (NaCl and $Na_2SO_4$) and the rhGH concentrations with the speed of the pH-change when passing the pI. The hydrodynamic radii of the particles in the dispersion of the peptide are changed from 2.4 to 0.22 nm. Hy stabilise the dispersion in changing its structure back to a curling like structure when pH is changed to pH 6. It is then possible to dilute the dispersions to the concentration desired. The hydrophobic properties of the peptide structure is found to be optimal as pH is changed in a strong acid solution pH<2 and by dialyses transferred to a neutral solution pH 6.

SUMMARY

HI-HPLC assays of none compact (n-compact.) and compact rhGH suggest activity of compact rhGH to be within acceptable limits and of the same magnitude as for of none compact rhGH. No agglomerates or particles are found upon dilution. Parental administration in H-x rats of Compact rhGH resulted in a dose response of growth gain and of Tibia elongation. None compact rhGH also resulted in a dose response of growth gain and of Tibia elongation in H-x rats.

The growth gain and the Tibia elongation were of similar magnitude for compact and none compact rhGH.

No growth gain or Tibia elongation was recorded for Placebo.

Conclusion

The structure of rhGH has been compacted. One rhGh unit has been compact from radii of 2.4 nm to 0.22 nm.

Full biological effect of compact rhGH is demonstrated in vivo. Hydrophobic properties of rhGH is obtained in acid solutions pH<2 and a durable hydrophobic structure is demonstrated when pH is changed to pH 6. The size and the hydrophobic properties of the complex suggest an improved oral bioavailability of rhGH.

DETAILED DESCRIPTION OF THE DRAWINGS

The present invention will be further described in more detail in the following figures, examples and tables.

EXAMPLE 1

Hy and pH-change

A substantial buffer capacity in aqueous Hy-solution was observed when diluted acids were added. Strong acid-solutions should be avoided due to breakdown of the polymer Hy–structure and also to loss of the acetyl-group. The time for studies of Hy with different plasmid/peptides should therefore be limited to around 30 min.

The particle size of Hy was studied upon pH-changes. Dynamic light scattering, 500 mV at Fysicum, Uppsala University, followed three concentrations of Hy 90, 30 and 10 μg/ml. Malvern, ZetaMaster S, version PCS: v 1.26 was also used to determine pH and $\xi$-potential The data from dynamic light scattering are presented in FIGS. 1–6. The figures are showing the correlation function and relaxation time distributions for the following concentrations of Hy:

10 μg/ml (with dilutions with water and acid to 5 μg/ml)
30 μg/ml (with dilutions with water and acid to 15 μg/ml)
90 μg/ml (with dilutions with water and acid to 45 μg/ml)

The resulting relaxation time distributions are essentially single-modal under all conditions. The peak width decreases systematically with increasing concentration due to a greater signal to noise ratio.

Figure 7:
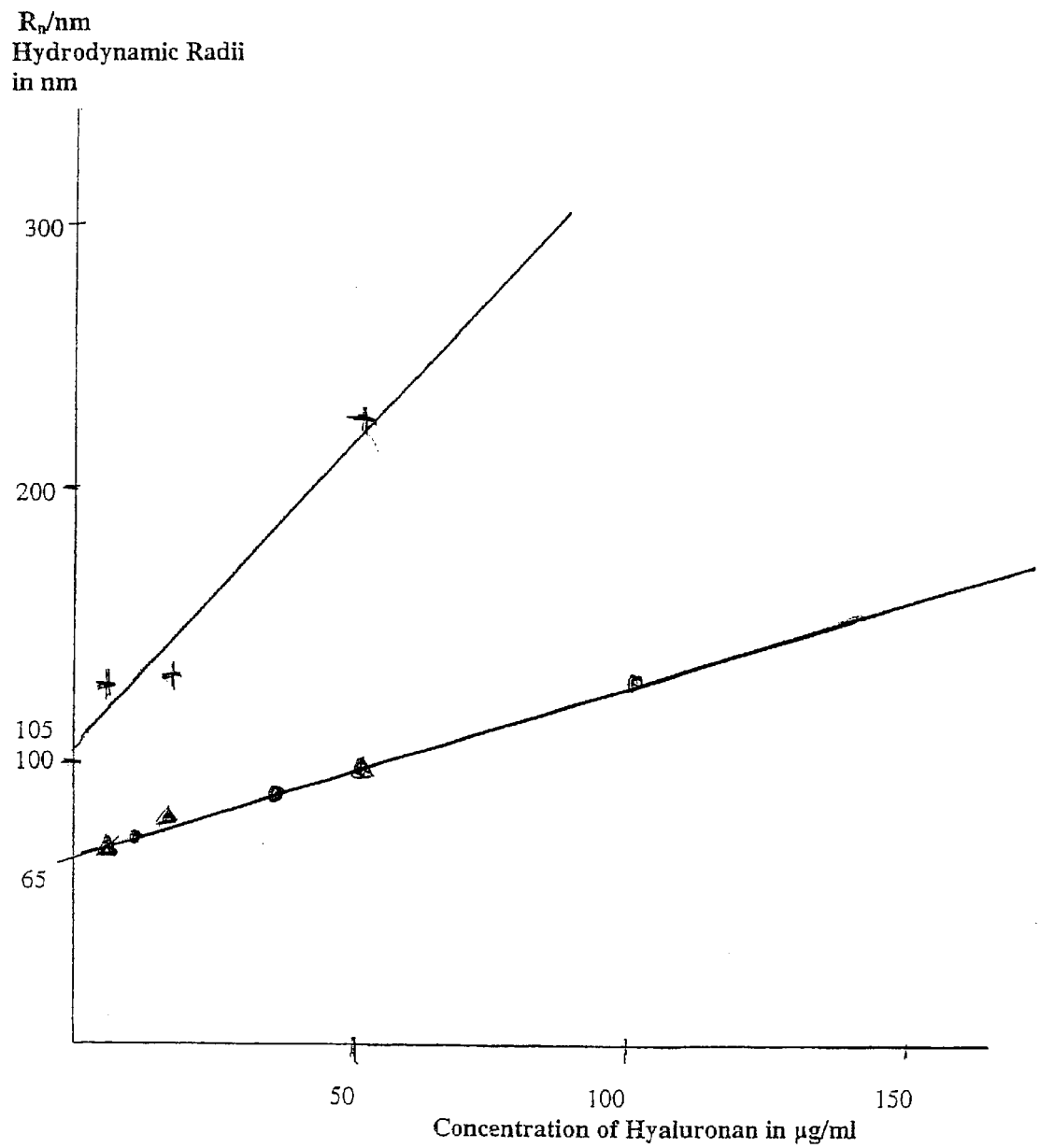
FIG. 7 is showing the hydrodynamic radii Rn in nm (0–300) as a function of the concentration of hyaluronic acid in μg/ml.

FIG. 7 is showing the hydrodynamic radii (Rn) in nm (0–300) as a function of concentration of Hy in μg/ml. The calculated hydrodynamic radii (FIG. 7) fall on the same line for the undiluted samples and those diluted with water. Those samples diluted with acid have considerably larger particle size. The true particle sizes in contrast to the apparent values which are influenced by interactions at finite concentrations are 65 nm (water solutions) and 105 (acid diluted). It is noteworthy that the scattered intensities are the same for the undiluted and water diluted samples, but about the double in value for the acid-diluted. For example, 11 kHz for the water-diluted and 26 kHz for the acid-diluted solutions. This is consistent with an increase in particle dimensions in acid-diluted solutions of Hy. This is indicative for that the Hy structure upon strong acid addition is stretching out from a curling cylinder to straight line.

pH, $\xi$-potential and hydrodynamic radii are presented in Table 1. The $\xi$-potential of the Hy– structure is changed from a negative charge (−59 mV) to positive charge (+3.1−+16.9 mV) as pH is changed from pH 6 to pH 1–2.

Conclusion: Hy with a molecular weight of 150 k Dalton becomes positively charged (3.1–16.9 mV) when pH changes from pH 6.5 to 1.5. Particle size measurements by dynamic light scattering 500 mV indicate that the Hy structure is stretching out from a curling cylinder to straight line upon addition of a strong acid. pH is changed from 6.5 to 1.5 and the hydrodynamic radii is almost doubled or changed from 65 to 105 nm.

TABLE 1

$\zeta$-potential, pH and hydrodynamic radii of Hy 150 k Dalton upon pH-changes.

| Hy in μg/ml | HCl 1 M in ml | Distilled Water in ml | pH separate measurement | Zeta Master, version PCS:v 1.26 | | | Lightscattering 500 mV Hydrodynamic radii in nm |
|---|---|---|---|---|---|---|---|
| | | | | KCPs | pH | $\zeta$-potential in mV | |
| 10 | — | 1 | 5.4–7.8 | 2844 | 6.5 | −59 | 65 |
| 10 | 1 | 1 | 1.4 | | 2.4 | 3.1 | — |
| 5 | 1 | 1 | 1.6 | 2542 | — | 16.9 | 105 |

TABLE 1-continued

ζ-potential, pH and hydrodynamic radii of Hy 150 k Dalton upon pH-changes.

| Hy in µg/ml | HCl 1 M in ml | Distilled Water in ml | pH separate measurement | Zeta Master, version PCS:v 1.26 | | | Lightscattering 500 mV Hydrodynamic radii in nm |
|---|---|---|---|---|---|---|---|
| | | | | KCPs | pH | ζ-potential in mV | |
| 30 | — | 1 | — | — | — | — | 65 |
| 15 | 1 | 1 | 2.3 | — | 2.5 | — | 105 |
| 90 | — | 1 | — | — | — | — | 65 |
| 45 | 1 | 1 | — | — | — | — | 105 |

EXAMPLE 2

Example 2 illustrates the mechanisms of Hy to obtain a durable compact plasmid. -DNA-structure.

The gene expression of the plasmid is encoded for Chloramphenicol Acetyl Transferace, CAT.

Solution 1: Plasmid pRc/CMV-CAT, double strained closed-ring structure ~6400 base pair, molecular weight 4250000 Dalton 200 µL was used in the concentration of 130 µg/ml.

Solution 2: 10.4 mg Hy molecular weight 150000 Dalton was dissolved in 100 ml water in a concentration of 104 µg/ml.

Solution 3: 2 M NaCl

Solution 3.1: 0.15 M NaCl was used

Solution 4: 1 M NaOH

Solution 5: 1 M HCl

The aimed final solution: 500 µl was formulated to contain

| | 500 µl | | | Conc. in µg/ml | (µg/µl) |
|---|---|---|---|---|---|
| pRc/CMV-CAT, | 200 µL | 0.13 µg/µl | 26 µg | 52 | (0.052) |
| Hy 150 Da | 50 µL | 0.1 µg/µl | 5 µg | 10 | (0.010) |
| Σ | 250 µL | | | | |

250 µL is diluted to 500 µL by pH shift pH 7.4/2.4 and precipitated by NaCl 2M.

Dialysing Procedure

Dialyse-tube, Spectra/Pore Membrane MWCO 6-9,000 Record No 132645

1. The tube is softened in distilled water for 1 h.
2. The tube is cut and a dialyse-claim is fitted at one edge of the tube.
3. 500 µL is filled in the bag. Filling is done with a sterile micro-pipette.
4. The other edge is fitted with a dialyse-claim.
5. The bag is dialysed for 30 h.
6. Control the integrity of the membrane.
7. The dialysed solution is sucked up with a sterile micro-pipette.
8. Control the volume in µL.

Preparation Steps

1. Thaw at 24° C. 200 µL of the plasmid solution 1 (0.13 µg/µl) 26 µg
2. Prepare positive charged Hy. pH of Solution 2 was checked; pH 8.33.
3. The pH-value of the Hy solutions were studied to obtain a positive ζ-potential of the Hy structure sees Table 2.

TABLE 2

Acidification of Hy

| Solution 2 in µL | 1 M HCl in µL | Hy in µg/ml | HCl in M | $pH_{Prim.}$ | $pH_{5\ min}$ | $pH_{30\ min}$ | $pH_{30\ min}$ |
|---|---|---|---|---|---|---|---|
| 2000 | 500 | 83.2 | 0.2 | 0.76 | ND | 0.68 | 0.81 |
| 2000 | 1000 | 69.3 | 0.33 | 5.19* | 2.28 | 2.93 | 2.9 |
| 2000 | 1500 | 59.4 | 0.42 | 0.37 | ND | 0.36 | 0.47 |
| 2000 | 2000 | 52 | 0.5 | 0.32 | ND | 0.26 | 0.39 |

*pH-value deviates from expected values and was therefore controlled.

TABLE 3

Control of deviating pH

| Solution 2 in μL | 1 M HCl in μL | Hy in μg/ml | HCl in M | pH$_{Prim}$ |
|---|---|---|---|---|
| 2000 | 1000 | 69.3 | 0.33 | 0.85 |
| 1000 | 50 | 99.0 | 0.047 | 1.18 |
| 1000 | 25 | 101.4 | 0.024 | 1.69 |

In example 1 it was found that in weak acid solutions the ζ-potential changes from a negatively to a positively charged structure (ζ-potential. from −69.3 to +8.9−+16.9 mV). The results were not consistent that is when the acidity goes towards a lower pH<pH 1.75 the measured ξ-potential indicate an increased negative charged structure of Hy (−4.4, −5.1, −17.9) see table 4.

TABLE 4

Positive charging of the Hy-structure

| Solution 2 in μL | 1 M HCl in μl | Hy in μg/ml | HCl in M | pH | KCPs | Zeta MasterS Version PCS:v1:26 n = 6 ζ-potential in mV |
|---|---|---|---|---|---|---|
| 2000 | 100 | 99 | 0.0476 | 1.3 | 2301 | −8.5 |
| 4000 | 100 | 101 | 0.0244 | 1.75 | 2241 | −4.4 |
| 2000 | 200 | 94.5 | 0.0909 | 1.08 | 2088 | −5.1 |
| 2000 | 1000 | 69.3 | 0.33 | 0.53 | 1900 | −17.5 |

Hy present in strong acid-solutions should be avoided due to a breakdown of the Hy structure and to a loss of the acetyl-group. The time to form a complex between Hy and different plasmid in strong acid solution should therefore be limited to around 30 min.

Solution to form a complex.

3. Hy solution, pH 1.75, is used in the studies to form a complex with the plasmid. Samples are dialyzed within 30 min against 0.15 M NaCl to rise the pH.

In this study 101 μg/ml Hy, pH 1.75, was chosen for preparing the compaction, although the measured ς-potential was negative. In solution 94.5 μg/ml Hy, pH 1.08 some measured values were positive but the values of 101 μg/ml Hy, pH 1.75, were more even contributed.

4. Mix 101 μg/ml Hy, pH 1.75, (0.11×101.4=11.1 μg Hy) or 110 μl Hy 11.1 μg Hy with Solution 1, Plasmid solution (pRc/CMV-CAT, 0.13 μg/μl) or 200 μL pRc/CMV-CAT, 26.0 μg plasmid
add within 30 min
Solution 3, 2 M NaCl 50 μl
add
Distilled. water 150 μl
Final solution Σ510 μl 4. Final solution 510 μl is incubated for 1 hour at 25° C.

5. Dialyzed against Solution 3.1, 0.15 M NaCl. The dialyze procedure and the membrane was checked 9 p.m. and 4 a.m. every day.

| Day 1 | 6 h. |
|---|---|
| Day 2 | 24 h |
| Day 3 | 24 h |
| Day 4 | 24 h |
| Day 5 | 13 h |
| Σ | 91 h |

| Hy-plasmid-complex is formulated to contain | 510 μL in μg | in μg/ml | in nM |
|---|---|---|---|
| pRc/CMV-CAT | 26 | 50.98 | 12.0 |
| Hy 150 000 Dalton | 11.1 | 21.76 | 145 |
| NaCl* | $2.1.4 \times 10^9$ | $4.2 \times 10^9$ | $150 \times 10^6$ |

*The concentration of NaCl is high and will be lowered in the coming studies

Physical-chemical Evaluation

Solution 1, plasmid pRc/CMV in 0.15 M NaCl (1+1) 130/2 μg/ml 30.57/2 pM).

Solution 2, Hya 150000 Dalton 104 μg/ml (69.3 pM) in distilled water.

The final solution the complex—(pRc/CMV-CAT+ Hy) 50.98+21.76 μg/ml in 0.15 m NaCl.

These were examined by Dynamic Light Scattering, Malvern Instruments England Zeta Master Version PCS: v1.26. The examined volume was ≈500 μL.

TABLE 5

Diameter by Volume (Diameter in nm.) of the Hy-plasmid-complex compared with plasmid pRc/CMV and Hy 150 000 Dalton.

| Solution used | Concentration in μg/ml | nM | Diameter by volume in nm |
|---|---|---|---|
| Hy 150 000 Dalton in water | 104 | 69.3 | 16.4[1)] |
| pRc/CMV-CAT in 0.15 M NaCl (1 + 1) | 65 | 15.25 | 87.1 $X_{n=6}$ |
| Complex-(pRc/CMV-CAT-Hy) in 0.15 M NaCl | 50.98 + 21.76 | 12.0 + 145 | 7.5 $X_{n=6}$ |

[1)]16.4 too low intensity of the laser for measurement

Conclusion the plasmid pRc/CMV-CAT has been compact from 87.1 nm to 7.5 nm.

The methods involve acidification, forming a complex, salting and dialyse treatment, at a molar ratio of plasmid/Hy 150000 Dalton 0.83–0.85:1.

Dynamic light scattering identifies the diameter of the complex pRc/CMV-CAT-Hy (7.5 nm).

Positive charging of the Hy- structure ($Hy_{pH\ 8.8}$ ζ-potential −51 to −69 mV $Hy_{pH\ 1.75}$ 1.6±2.3 mV), PH-shift (pH<2 pH 6) and an ionic concentration change of NaCl 2 M to 0.075 M forms the complex.

It is indicated that the compact state of the complex is persistent after storage 3 months at 5–8 C.

EXAMPLE 3

Objective Preparation of a plasmid—Hyaluronan complex for transfection studies in cells and physicochemical characterisation after three (3) months of storage.

Preparation is done with a newly prepared plasmid (conc.0.67 μg/ml) with the following changes; a new molar ratio plasmid/Hy 0.1128 (molar ratio plasmid/Hy 0.085), batch size 1020 μl (520 μl), pH 1.65 and 1.8 (pH 1.75 and 1.08).

Results The complexion is based on a positive charging of the Hyaluronan (Hy) structure ($HY_{Dest.\ w.}$ ς−61.5±8.5 mV/$Hy\varsigma_{pH}$ 1.65 −2.4±2.2 mV, $HY_{Dest.\ w.}$ ς−61.5±8.5 mV/$Hy\varsigma_{pH}$ 1.80 −4.0 mV±1.9 mV) The complex is formed by a pH-shift (pH≦2/≡6,) and an ionic concentration change (NaCl 2 M /0.075M). The Plasmid-Hy complex is determined after 3 months of storage at 5–8° C. and characterised by a plasmid compression of the plasmid from 356 (98.9–507) nm at pH-shift 1.65≧6.0 to 84.41 nm at pH-shift 1.80≧6.0 to 69.0 nm identified by dynamic light scattering (see Table 6)

Solution 3; 2 M NaCl
Solution 3.1; 0.15 M NaCl
Solution 3.2; 0.075 M NaCl
Solution 4; 1 M NaOH
Solution 5; 1 M HCl All chemicals were of analytical grade P.A. Solutions Titrisol Merck Dialyze-tube, Spectra/Poor Membrane MWCO 6-9,000 Record No 132645

Operating and checking the dialyse-tube.
1. The tube is softened in distilled water for 1 h.
2. The tube is cut and a dialyse-claim is fitted at one edge of the tube.
3. 500 μL is filled in the bag. Filling is done with a sterile Micropipette.
4. The other edge is fitted with a dialyse-claim
5. The bag is dialysed for 30 h.
6. Control the integrity of the membrane.
7. The dialysed solution is sucked up with sterile Micropipette tubes.
8. The volume is controlled and given in μl.

Preparation Steps

Containers for the final solutions, pipettes, pipette tubes, beakers, holders for tubes and other materials were sterilised according to Autoclave program.

The preparation steps were performed under aseptic conditions in a Laminar Air Flow (LAF-) cabinet, LAF Holten HB 2472 S.

TABLE 6

Solutions prepared for transfection studies and particle size determination of these

| | Plasmid-complex formed by pH shift 1.65 ≧ 6.0 Hy $\varsigma_{pH1.65}$ −2.4 ± 2.2 mV | | | Plasmid-complex formed by pH shift 1.8 ≧ 6.0 Hy $\varsigma_{pH1.80}$ −4.0 mV ± 1.9 mV | | | Naked plasmid at pH 6.0 | | | Hy 104 μg/ml in Dist. w. ζ −61.5 ± 8.5 mV | |
|---|---|---|---|---|---|---|---|---|---|---|---|
| Complex/ Plasmid/Hy | 1020 μL in in μg | in μg/ml | in nM | 1020 μL in in μg | in μg/ml | in nM | 1020 μL in in μg | in μg/ml | in nM | in μg/ml | in nM |
| pRc/CMV-CAT + Hy | 72 + 22.52 | 70.58 + 22.08 | 16.6 + 147.2 | 72 + 22.66 | 70.58 + 22.2 | 16.6 + 148.1 | — | — | — | 105 | 700 |
| pRc.CMV-CAT | — | — | — | — | — | — | 72 | 70.6 | 16.6 | — | — |
| NaCl | 2.23 $10^3$ | 4.38 $10^3$ | 75 $10^6$ | 2.23 $10^3$ | 4.38 $10^3$ | 75 $10^6$ | 2.23 $10^3$ | 4.38 $10^3$ | 75 $10^6$ | — | — |
| Particle size Diameter by volume in nm | 84.41 | | | 69.0 | | | 98.9–507 | | | 98.9 ± 43.1 | |

Conclusions an optimal molar ratio for the plasmid compression was not found in. After storage 3 months at 5–8° C. the molar ratio plasmid/Hy 0.1128 resulted in compression from 98.9–507 nm to 69.0 at pH 1.8 and to 84.41 nm at pH 1.65. For a molar ratio plasmid/Hy 0.085 the plasmid was compressed from 87 nm to 7.5 nm at pH 1.75. It is also indicated that the new plasmid was impure that is a two size distribution with a peak at 98.9 and one peak at 507 nm.

Experimental Material

Solution 1: Plasmid pRc/CMV-CAT molecular weight 4250 kDa, concentration 0.67 μg/μL. The original plasmid concentrate is diluted in dist. w. to a concentration of 0.194 μg/μL and frozen at −22° C.

Solution 2; 10.5 mg Hy mol. wt. 150 kDa was dissolved in 100.0 ml Dist. water. Concentration 105 μg/ml Three different plasmid solutions were prepared Plasmid-Complex formed by pH shift 1.65(1.63–1.67)≧6.0, by pH shift 1.80 (1.78–1.79)≧6.0 and the naked plasmid at pH 6.0.

1. Thaw at 24° C., 9 frozen (−24° C.) tubes containing ≡139 μL (0.194 μg/μl) of the plasmid, "Solution 1". 372. μl or 72. μg (372 μL×0.194 μg/μL=72 μg) was used (52 μg will be needed since 26 μg was used to prepare 510 μg and resulted in a good compression.

2. Prepare the pH-adjusted Hy-solutions. Start time=0 (Total time for preparation steps 2,3,4 and 5 should be limited)

Hy-solutions pH 1.65 Hy-solutions pH 1.8 4000 μL Hy-solution 105 μg/ml 4000 μl Hy-solution, 105 μg/ml 100 μL 1M HCl (approximate amount 75 μL 1M HCl Pipette out of order)

The solutions were mixed for 20 min magnetic stirring, low speed. The pH and the ξ-potential were checked. For control of the ξ-potential the solutions were placed in a refrigerator tor at 5–8° C. and the ς-potential was measured 5 days later Concentration of Hy; 102.4 μg/ml Concentration of Hy; 103 μg/ml pH; 1.63–1.67 at 24° C. pH; 1.78, 1.79 at 24° C.

HY $\varsigma_{pH}$ 1.65; −2.4±2.2 mV Hy $\varsigma_{pH}$ 1.8; −4.0±1.9 mV Time used 30 min 3. Mix the plasmid with the Hy-solution by magnetic stirring low speed. Measure the time spend for the preparation Time used 30 min,$\Sigma_{2,3}$ 60 min 4. Add 2 M NaCl and Dist. w. and incubate the solutions above at 24° C. for 30 min Low magnetic stirring Time used 26 min$\Sigma_{2,3,4}$ 86 min

TABLE 7

Preparation of the plasmid-complexes and the naked plasmid, step 3, 4; time used 56 min

| Plasmid-complex formed at pH 1.65 Hy $\zeta_{pH\ 1.65}$ −2.4 ± 2.2 mV | | Plasmid-complex formed at pH 1.8 Hy $\zeta_{pH\ 1.8}$ −4.0 ± 1.9 mV | | Naked plasmid at pH 6.0 $\zeta_{pH\ 6.0}$ N.D. | |
|---|---|---|---|---|---|
| Hy-solution pH 1.65 | 220 μL | Hy-solution pH 1.8 | 220 μL | | |
| Plasmid 0.194 ug/ul | 372 μL | Plasmid 0.194 ug/ul | 372 μL | Plasmid 0.194 ug/ul | 372 μL |
| 2 M NaCl | 100 μL | 2 M NaCl | 100 μL | 2 M NaCl | 100 μL |
| Dist .w. | 328 μL | Dist .w. | 328 μL | Dist .w. | 548 μL |
| Total amount | 1020 μL | Total amount | 1020 μL | Total amount | 1020 μL |

5. Stabilise the complexes by a pH-shift (pH ≦2/≡6,) and an ionic concentration change (NaCl, 2M/0.075M). The total time for preparation steps 3,4 and 5 should be limited to 30 min from starting time.

Aseptic transfer and close 1020 μL Plasmid-complex formed at pH 1.65, 1020 μl Plasmid-complex formed at pH 1.8 and 1020 μL Naked plasmid at pH 6 into the dialyse tubes according to handling direction.

Place the closed tubes into a dialyse-bath containing 1000 ml 0.075 M NaCl. Start the magnetic stirring. Record the dialyse-time.

Time used to dispense the solutions 45 min Total time used step 3–5, 131 min.

6 Dialyse the tubes (48 h, change of 0.075 M NaCl, twice) Dialyse Procedure 6.1 The closed tubes were dialysed at 24° C. in 0.075 M NaCl 1000 ml for 44 h, magnetic stirring.

6.2 The solution in the dialyse-bath was renewed 0.075 M NaCl 1000 ml and the closed tubes were placed into a dialyse-bath for 4 h at 24° C. magnetic stirring

TABLE 8

Solutions (Plasmid-complex and plasmid) for transfection studies are formulated to contain

| (pRc/CMV-CAT + Hy) in 75 mM NaCl Complex formed by pH shift 1.65 ≧ 6.0 Hy $\zeta_{pH\ 1.65}$ −2.4 ± 2.2 mV | | | (pRc/CMV-CAT + Hy) in 75 mM NaCl Complex formed by pH shift 1.8 ≧ 6.0 Hy $\zeta_{pH\ 1.8}$ −4.0 ± 1.9 mV | | | pRc/CMV-CAT in 75 mM NaCl pH 6.0 | | |
|---|---|---|---|---|---|---|---|---|
| 1020 μL in μg | in μg/ml | in nM | 1020 μL in μg | in μg/ml | in nM | 1020 μl in μg | in μg/ml | in nM |
| 72 + 22.52 | 70.58 + 22.08 | 16.6 + 147.2 | 72 + 22.66 | 70.58 + 22.2 | 16.6 + 148.1 | 72 | 70.6 | 16.6 |

7 Aseptic dispense the solutions into sterilized tubes with sterile Micro-pipette tubes in portions of 100 μL to fill tubes in an amount of 500 μL* 2

8 Measure the volume obtained, determine the pH-values with pH-paper-indicator and label the tubes with date for ready-packed and signature

TABLE 9

| | Volume obtained, pH and label | |
|---|---|---|
| Volume obtained in μl pH of plasmid-complex formed at pH shift 1.65 ≧ 6.0 Label | Volume obtained in μl pH of plasmid-complex formed at pH shift 1.8 ≧ 6.0 Label | Volume obtained in μl pH of naked plasmid Label |
| 500/150 Σ 650 6.0 pRc/CMV-CAT-Hy Complex .pH 1.65/6.0 | 500/250 Σ 750 6.0 pRc/CMV-CAT-Hy Complex .pH 1.8/6.0 | 500/300 Σ 800 6.0 pRc/CMV-CAT .pH 6.0 |

9. Store the plasmid-solutions at 5–8° C. in a dark place.

Physical-chemical Evaluation

Positive charging of Hy Determination of pH, ζ-potential and particle size for Hy 150 k D

TABLE 10

| | | | Determination of pH, ζ-potential and particle size for Hy 150 000 Dalton | | | | | |
|---|---|---|---|---|---|---|---|---|
| Hy 150 000 Dalton Conc. in μg/ml | Additives in nM | pH in M | ZetaMasterS Version PCS:v1.26 mean of 6 measurements | KCPs | ζ-potential in mV | KCPs | Particle size Diameter by ZA ve in nm | Diameter by volume in nm |
| 105 | 700 | Dist. water | | 7.0–7.5 | 1694 | −61.5 ± 8.5 | 0.5 | 116.5 ± 51 | 98.9 ± 43.1 |
| 103 | 687 | HCl | 0.0184 | 1.80 | 1890 | −4.0 ± 1.9 | 0.4 | 112.5 ± 89.9 | 128.5 ± 31.1 |
| 102.4 | 683 | HCl | 0.0244 | 1.65 | 2108 | −2.4 ± 2.2 | N.D. | N.D. | N.D. |

TABLE 11

| | Diameter by volume of the Hy-plasmid-complex compared with plasmid pRc/CMV-CAT and Hy 150 KDa storage 3 months 8° C. | | |
|---|---|---|---|
| Preparation examined | Concentration in μg/ml | nM | Diameter by volume $X_{n-6}$ in nm |
| Hy 150 KDa in Dist w pH 7.0–7.5 | 105 | 700 | 98.9 ± 43.1 |
| Hy 150 KDa in Dist w pH 1.80 | 103 | 687 | 128.5 ± 31.1 |
| pRc/CMV-CAT in 0.038 M NaCl pH ≅ 6 | 97 | 22.82 | 98.9/507 |
| Complex-(pRc/CMV-CAT + Hy) in 0.075 M NaCl pH 1.65 ≧ 6 | 70.58+ 102.4 | 16.6 + 683 | 84.41** |
| Complex-(pRc/CMV-CAT + Hy) in 0.075 M NaCl pH 1.8 ≧ 6 | 70.58+ 103 | 16.6 + 687 | 69.0** |

*Values are deviating; indicating two different particle sizes see Table 12
**Prime values (Storage, 3 months 8° C.) see Table 8

TABLE 12

Determination of pH and the particle size for plasmid pRc/CMV-CAT

| Plasmid Conc. 0.0375 M NaCl | | | | ZetaMasterS Version PCS:v1.26 mean of 6 measurements | |
|---|---|---|---|---|---|
| in µg/ml | in nM | pH | KCPs | Particle size ZA ve in nm | diameter by volume in nm |
| 97 | 22.8 | 6 | 1.3 ± 0.1 | 258.5 ± 111.8 | N.D. |
| 97 | 22.8 | 6 | 0.8 ± 0.2 | 100 ± 33 | 98.9–507 |

TABLE 13

Determination of the particle size of the plasmid-complex formed by pH shift 1.65 ≧ 6.0 and 1.8 ≧ 6.0 in 0.075 M NaCl after storage 3 month at 8° C.

| Plasmid Conc. 0.075 M NaCl | | | | ZetaMasterS Version PCS:v1.26 mean of 6 measurements | |
|---|---|---|---|---|---|
| in µg/ml | in nM | pH shift | KCPs | Particle size ZA ve in nm | diameter by volume in nm |
| 70.58 | 16.6 | 1.65 ≧ 6.0 | 1.4 ± 0.2 | 60.6 ± 9.3 | 84.41 |
| 70.58 | 16.6 | 1.8 ≧ 6.0 | 1.4 ± 0.1 | 55.8 ± 18.1 | 69.0 |

EXAMPLE 4

This example illustrates the influence pH-changes have on the compaction and the solubility of peptides. It also shows on methods to determine solubility.

Solubility of peptides was examined as a function of pH. The peptides were concentrated by ultra centrifugation at pH 8 and dialysed towards different pH. For solubility evaluation the dialysate in the dialyse-tube was kept in equilibrium with a precipitate of the peptide at different pH for 24 hours at 20° C. The precipitate was removed and the solution was filtered through a 0,22 µm membrane filter. The concentration was determined by UV absorption at 276 nm. Different buffer systems were used for solubility determination at different pH. These data are used for dissolving and compacting peptides at different pH.

Figure 8:
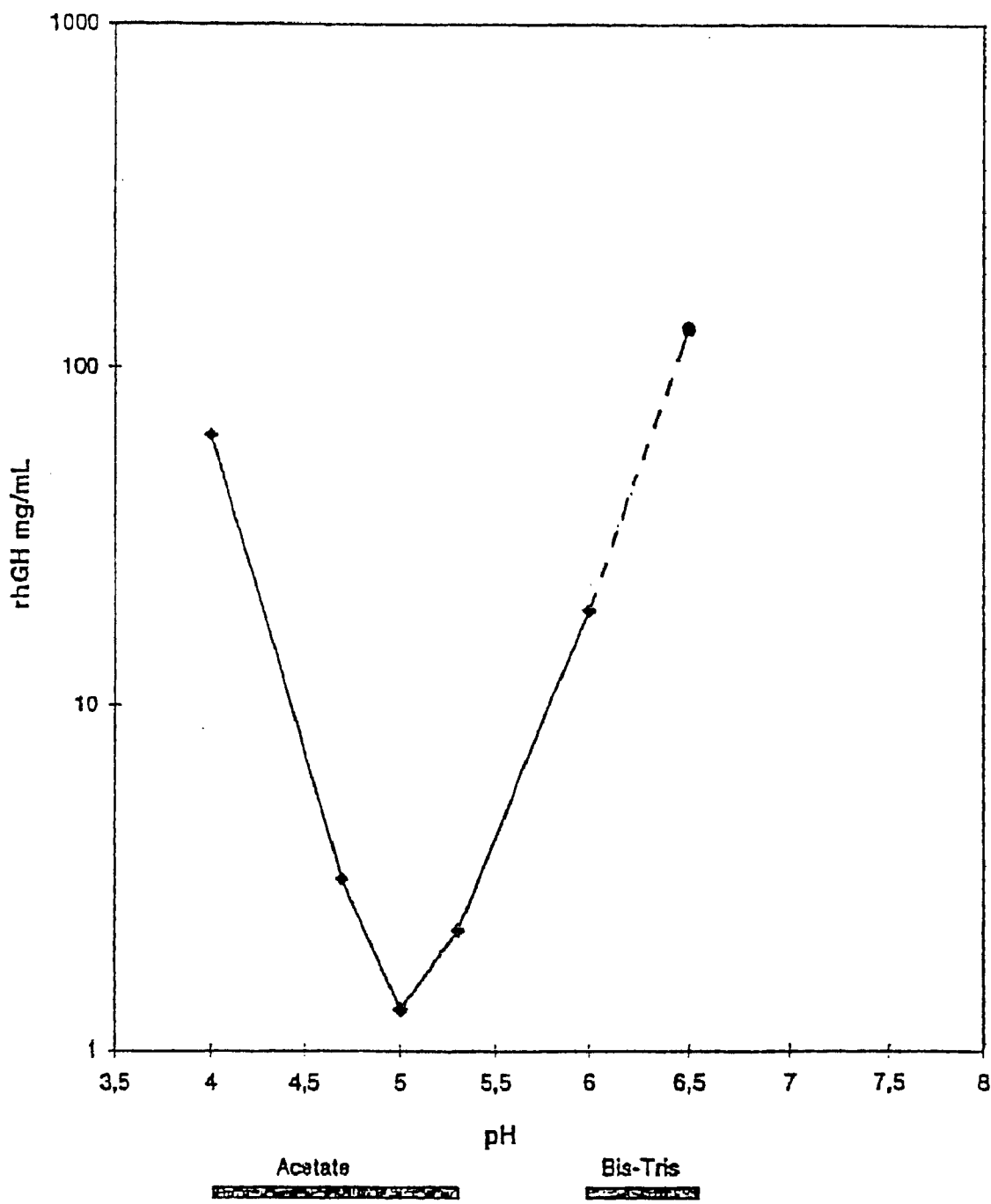
FIG. 8 is illustrating the solubility of rhGH.

Recombinant growth hormone 33 mg/ml was used for solubility determination. A minimum of solubility was found at pH 5.0 around 1 mg/ml. This occurs at the iso-electric point (pI). On both sides of this pH the solubility for rhGH rose sharply. At pH 7.5 rhGH could be concentrated in a Tris-HCl buffer to 160 mg/ml In a sodium-acetate buffer pH 4.0 a concentration of 62.6 mg/ml was observed. On the acid-side of pI equilibrium of clear solutions and precipitates were found indicating that rhGhH only consist of one genuine form. This in comparison to the base-side where colloid dispersions co-exists with clear solutions of rhGH. Different and diverting clarity of rhGH solutions on the base-side indicate polymorph forms of rhGH. Solubility of rhGH is illustrated in FIG. 8 and Table 14

TABLE 14 dialysis of rhGH in buffers of different pH.

| Buffer (25 mM) | pH, measured in dialysis sample | Conditions in dialysis sack after equilibrium | Concentration of rhGH after filtration (mg/mL) |
|---|---|---|---|
| Na-acetat pH 4.5 | 4.0 | Precipitate | 62.6 |
| Na-acetat pH 4.7 | 4.7 | Precipitate | 3.1 |
| Na-acetat pH 5.0 | 5.0 | Precipitate | 1.3 |
| Na-acetat pH 5.3 | 5.3 | Precipitater | 2.2 |
| Bis-Tris pH 6.0 | 6.0 | Precipitate/gel | 18.9 |
| Bis-Tris pH 6.5 | 6.5 | Slightly opalescent | 129.3 |

Conclusion Equilibrium of clear solutions and precipitates were found on the acid-side of pI, indicating that rhGH only exists in one genuine form at this pH. A minimum of solubility, 0.1 mg/ml was found at pH 5. On the base-side of pI colloid dispersions co-exists with clear solutions indicating polymorph forms of rhGH. These observations were used to get a homogenous precipitate of rhGH when condensing rhGH. This procedure involves the dissolution in an acid environment of a high concentration of rhGH, the dialysing of the solution throughout pI and the stabilising of the precipitate by a polymer. The stabilised suspension is then transferred in the polymeric-form to a pH not exceeding pH 6–6.5.

EXAMPLE 5

This example shows how to improve the hydrophobicity of a peptide structure. The hydrophobicity is gained in an acid solution with pH on the acid-side of its pI. Two different forms of rhGH were observed in a study to determine buffer capacity. One a deprotonised form was obtained in an acid solution. The other a protonised form was obtained in an alkaline solution. The deprotonised form of rhGH was found to have a stronger proton binding capacity compared to protonised rhGH. A more nonpolar character of the protonised rhGH compared to deprotonize rhGH the former burying the polar groups explains this.

Recombinant Human Growth Hormone (rhGH molar mass 22124) used in the study was concentrated on DEAE-FF-gel (Pharmacia Biotech AB) and desalted on Sephadex G 25 gel (Pharmacia Biotech AB) to contain 33.3 mg/ml in distilled water. Hydrophobic Interaction Chromatography (HIC) was used to determine purity of rhGH 99.2%. The buffer capacity of rhGH was determined by potentiometric acid-base titration. By adding acid and base to the peptide a protonised and a deprotonised form of rhGH is obtained. These forms are then titrated back with base and acid.

Figure 9:
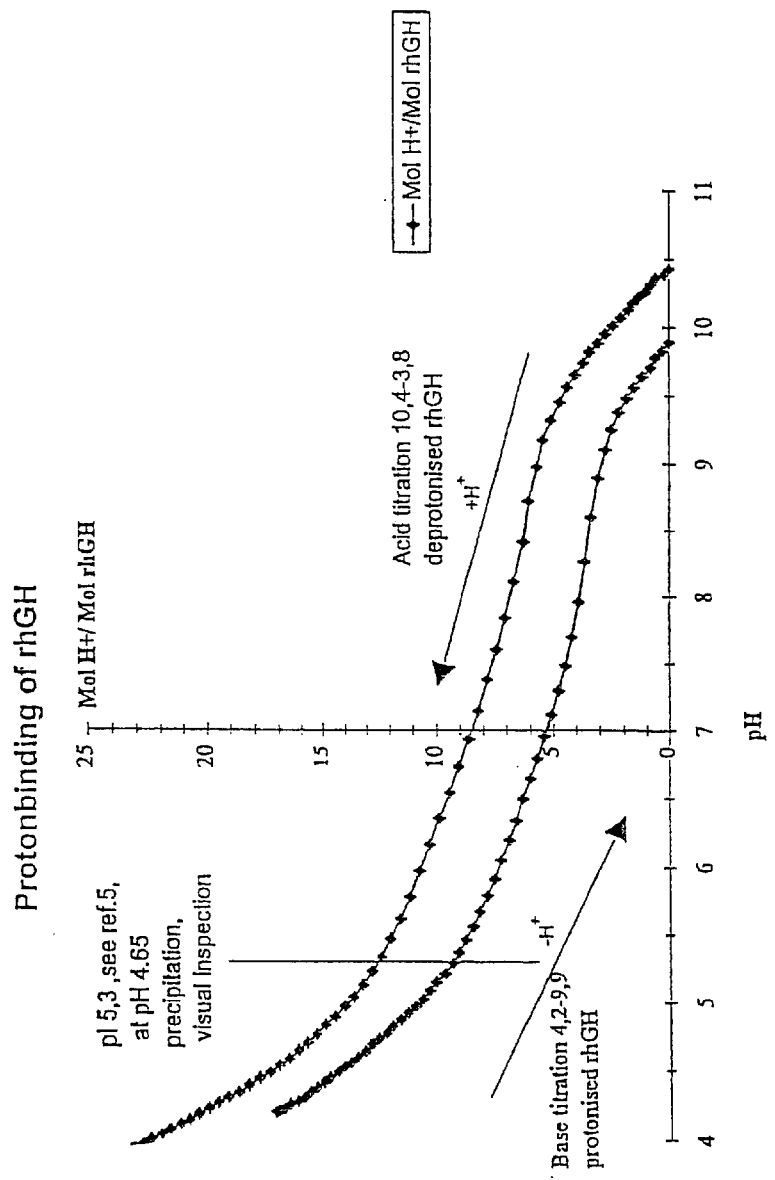
FIG. 9 is illustrating the proton-binding capacity of rhGH as a function of pH.

It was found that the proton binding capacity is stronger for the deprotonised form of rhGH compared to the protonised rhGH. A more nonpolar character explains a lesser uptake of protons by the protonised rhGH burying its polar groups. This property a more nonpolar character of a peptide resulting in a more hydrophobic character is used to improve the oral bio-availability. This is done by bringing the peptides in an acid state at pH~1 and keeping it where for about one hour and transferring it back to pH 6.5. Graphic presentation of the protonbinding of deprotonised and protonised rhGH is illustrated in FIG. 9. FIG. 9 is illustrating the proton binding capacity of rhGH as a function of pH, suggesting that protonised rhGH (at the acid side) is more hydrophobic when protonised rhGH (at the base side). In changing the pH in the interval 4–10 a precipitation and cloudiness is seen in the interval 4.6–5.0. Above pH 9.0 a slight cloudiness is seen indicating that clear solution of rhGH are obtained in a pH interval 6.5–8.5. This property a clear solution is used in judging time for dialysing a Compact rhGH, see Example 6 and 7.

Conclusion: Acidification of peptides is here used to get a hydrophobic state of the peptide and to improve its oral bio-availability.

EXAMPLE 6

This example illustrates the compaction of rhGH. By changing pH to a strong acid-solution (pH 1.5) Hy becomes charged stretching out from a curling cylinder to straight line. At this pH rhGH is easily soluble. The size of the rhGH particles is moderated by the speed of the pH-change and the ionic concentration change from 2 M to 0.15 M NaCl. The pH-interval used is 7–1.5–5.0(pI) at a constant ratio of rhGH: Hy. Hy stabilise the dispersion in changing its structure back to curling like structure at pH 6–7.

The preparations were assayed with HI-HPLC. The particle size of the Compact and the None Compact rhGH was determined after storage at 5–8° C. for 30 days by light scattering, Z-master. The diameter of the measured particles is given in means of six measurements.

Preparation:Compact rhGH 20.78 mg Hy with a molar mass of 150 KDa was dissolved in 900 μl distilled water and was allowed to react for more than 1 hour.

The pH 9.2 of the Hy-solution was adjusted to pH 1.51 with 50 l water and 50 μl 1 M HCl.

30.65 mg of lyophilised rhGH was dissolved in the Hy-solution. The molar ratio rhGH: Hy is 10:1. In portions of 10 μl 1 M HCl was added to obtain a clear solution and to change pH in the solution from 1.7 to 1.48 at that pH the solution was clear. The final volume was 1000 μl. The solutions were divided in two parts and transferred in two bags prepared as a dialyse tube of MWCO 6-8000, Spectra Pore R. softened in a tris buffer 10 mM pH 7.8 for 24 hours.

None Compact RHGH 30.7 mg rhGH was dissolved in 990 μl distilled water pH 7.4 the final volume of the solution pH 7.0 was adjusted to 1000 μL. The solution was divided in two parts and transferred in two bags (Bag1, Bag2) softened in a tris buffer 10 mM pH 7.8 for 24 hours.

Dialyse Procedure

The tubes were dialysed in tris—Buffer 10-mM pH 7.9. The solution, volume 600-ml, was exchanged 3 times. Dialyse Procedure MWCO 6-8000, Spectra Pore R

TABLE 15

| | | Compact rhGH | | | | None Compact rhGH | | | |
|---|---|---|---|---|---|---|---|---|---|
| Experiment# | | $4_1$ (Bag 1) | | $4_1$ (Bag 2) | | 4, (Bag 1) | | 4, (Bag 2) | |
| Dialyse time in hour | pH in Dialyse Solution | pH | Ocular/ volume in μl | pH | Ocular/ volume in μl | pH | Ocular/ volume in μl | pH | Ocular/ volume in μl |
| 0 | 7.9 | 1.5 | Clear/ 500 | 1.5 | Clear/ 500 | 1.5 | Clear 500 | 1.5 | Clear 500 |
| 1 | 7.4 | N.D. | precipitate | N.D | precipitate | N.D. | Clear | N.D. | Clear |
| 19 | 7.4 | N.D. | Cake in Solution | N.D. | Particles in Solution | N.D. | Clear | N.D. | Clear |
| 42 | 7.8 | 7.4 | Cake in Solution 300 | 7.4 | Particles in solution 750 | 7.6 | Clear/ 200 | 7.6 | Clear/ 200 |

The above-prepared Compact rhGH and None Compact rhGH are used for analytical assay (in situ determined biological activity and for particle sizing. The concentrations used for particle sizing of Compact rhGH was 7.6 mg/ml and 9.3 mg/ml and for None Compact rhGH 15 mg/ml. The measurements, means of six measurements were done at 25° C.

Result

Analytical Assay, HI-HPLC of Compact and of None Compact rhGH HI-HPLC assay is commonly used to determine biological activity of rhGH

TABLE 16

| Preparation | Compact rhGH | | None Compact rhGH |
|---|---|---|---|
| Experiment # | $4_1$ Bag 1 | $4_1$ Bag 2 | 4 (Bag 1 + 2) |
| Quantitative Assay, mg/ml | 7.6 | 9.3 | 15.2 |
| Monomer in % | 97.3 | 93.8 | 98.3 |
| LMWG, % | 0.8 | 0.7 | 0.7 |
| Clipped Forms in % | 1.9 | 5.5 | 0.9 |
| Retention Time, min | Approved | Approved | Approved |
| pH in dialyze-tube | 7.4 | 7.4 | 7.6 |
| Appearance in dialyze-tube | cake | particles | clear |

Conclusion: The values obtained for compact rhGH, $4_1$ Bag1 and $4_1$ Bag 2, Table 1, are within limits for an approved biological activity. Values are also of the same magnitude as for the untreated peptide, none compact rhGH. This suggests that the procedure to compact rhGH does not change the biological activity of rhGH as determine with HI-HPLC-method.

Particle sizing of Compact and of None Compact rhGH was performed by light scattering, Z-master.

TABLE 17

| | Particle size of Compact rhGH diluted 1:10 Diameter by volume in nm | | Particle size of None Compact rhGH diluted 1:10 Diameter by volume in nm |
|---|---|---|---|
| Preparation | | | |
| Experiment # | $4_1$ Bag 1 | $4_1$ Bag 2 | 4 Bag 1 + 2 |
| Colloidal | 23.1 | 23.3 | 75 |

TABLE 17-continued

| Preparation | Particle size of Compact rhGH diluted 1:10 Diameter by volume in nm | | Particle size of None Compact rhGH diluted 1:10 Diameter by volume in nm |
|---|---|---|---|
| solution | | | |
| Cake in equilibrium with a solute | N/A | 114 | N/A |

Conclusion: The values obtained of the diameter by volume for None Compact rhGH and Compact rhGH indicate that for Compact rhGH the diameter is changed from 75 nm to 23 nm and that a cake or particles are obtained. This suggests that the procedure to compact rhGH lessen the particle size of rhGH

EXAMPLE 7

This example illustrates the biological activity of Compact and None Compact rhGH in rats with ectomised hypophysis (Hx-rats).

For optimising the compaction of the rhGH structure the ionic concentration was altered from 2 M to 0.15 M NaCl * in Example 6 to in Example 7 1 M $[NH_4]_2SO_4$ dialysed against 0.15 M NaCl**, and to 1 M $Na_2SO_4$ dialysed against 0.15 M NaCl. The following anions; phosphates chlorine acetate and cat ions; $NH_4$, potassium, magnesium were also evaluated. Only $Na_2SO_4$ was considered for further studies. The preparations were assayed by HI-HPLC-technique. The particle size of compact and none compact rhGH was determined With DynaPro-801 after storage at 5–8° C. for 21 days.

* "2 M/0.15 M NaCl" The solutions ionic properties are changed from 2 M to 0.15 M by dialyse.
**1 M $[NH_4]_2SO_4$ was found to give a heavy precipitation and therefore omitted.

Low dose, 0.04 IU/ml, and high dose, 0.16 IU/ml, of compact and none compact rhGH were compared in Hx-rats to confirm biological activity and to examine an expected dose-response. A group of the Hx-rats were also treated with a placebo solution***.

*** Bovine albumin 12.5 ml (200 mg/ml) was diluted with iso-tonic NaCl to 1000 ml. This solution, Diluent 1.25% Albumin, was used as placebo and to dilute the solutions of Compact rhGH and None Compact rhGH in doses for animal trials.

Preparation Compact rhGH 14.9 mg Hy with a molar mass of 150 KDa was dissolved in 1200 µl 1 M $Na_2SO_4$ and was allowed to react for more than 1 hour The pH of the Hy-solution pH 7.6 was adjusted to pH 1.51 with 100 µl water and 330 µl HCl 1 M to a clear solution. HCl was added slowly when passing pH 3.8 a precipitate was observed. 22 mg of lyophilised rhGH was dissolved in the Hy-solution. The molar ratio rhGH: Hy is 10:1. In portions of 10 µl 1M HCl was added to obtain a clear solution. pH at start is 2.77. 40 µl of 1 M HCl was added to change pH in the solution from 2.77 to 1.52.

The solution was not totally clear. A loss of the solution was obtained when transferred to the dialyse bag. The final volume was 1240 µl. The solutions were divided in two parts and transferred in two bags prepared as a dialyse tube of MWCO 6-8000, Spectra Pore R. softened in a tris buffer 10 mM pH 7.8.

None Compact RHGH 22 mg rhGH was dissolved in 990 µl distilled water pH 7.4. The final volume of the solution was adjusted to 1240 µL. The solution was divided in two parts and transferred in two bags (Bag1, Bag2) softened in a tris buffer 10 mM pH 7.8.

Dialyse Procedure

The tubes were dialysed in tris—Buffer 10-mM pH 7.9. The solution, volume 600-ml, was exchanged 3 times.

TABLE 18

| | | Dialyse Procedure MWCO 6-8000, Spectra Pore R | | | | | | | |
|---|---|---|---|---|---|---|---|---|---|
| | | Compact rhGH | | | | None Compact rhGH | | | |
| Experiment# | | $5_1$ (Bag 1) | | $5_1$ (Bag 2) | | 5 (Bag 1) | | 5 (Bag 2) | |
| Dialyse time in hour | pH in Dialyse Solution | pH | Ocular/ volume in µl | pH | Ocular/ volume in µl | pH | Ocular/ volume in µl | pH | Ocular/ volume in µl |
| 0 | 7.9 | 1.5 | Clear/ 620 | 1.5 | Clear/ 620 | 1.5 | Clear 620 | 1.5 | Clear 620 |
| 19 | 7.4 | N.D. | precipitate | N.D | precipitate | N.D. | Clear | N.D. | Clear |
| 24 | 7.5 | N.D. | Cloudy | N.D. | precipitate | N.D | Clear | N.D. | Clear |
| 42 | 7.6 | 7.3 | almost clear 420 | 7.3 | almost clear 1100 | 7.6 | Clear/ 550 | 7.4 | Clear/ 450 |

The above-prepared Compact rhGH and None Compact rhGH are used for analytical assay (in situ determined biological activity), in vivo biological activity and for particle sizing.

The concentrations used for particle sizing of Compact rhGH were 5,3 mg and 1.5 mg and for None Compact rhGH 5–10 mg. The sizing is given in means of ten measurements and was done at 18, 25 and 30° C.

Result

Analytical Assay, HI-HPLC of Compact and of None Compact rhGH HI-HPLC assay is commonly used to determine biological activity of rhGH.

TABLE 19

|  | Compact rhGH | | | None Compact rhGH | |
|---|---|---|---|---|---|
| Preparation Experiment # | $4_1$ (Bag 1) | $4_1$ (Bag 2) | $5_1$ (Bag 1 + 2) | 4 (Bag 1 + 2) | 5 (Bag 1 + 2) |
| Quantitative Assay, mg/ml | 7.6 | 9.3 | 5.3 | 15.2 | 14.2 |
| Monomer, % | 97.3 | 93.8 | 100 | 98.3 | 98 |
| LMWG, % | 0.8 | 0.7 | <0.3 | 0.7 | 0.6 |
| Clipped forms, % | 1.9 | 5.5 | <0.2 | 0.9 | 0.2 |
| Retention Time, min | Approved | Approved | Approved | Approved | Approved |
| pH in dialyse-tube | 7.4 | 7.4 | 7.3 | 7.6 | 7.4 |
| Appearance in dialyse-tube | cake | particles | almost clear | clear | clear |
| Volume of clear solution in µl | 300 | 750 | 1520 | 400 | 1000 |

Conclusion: The values obtained for compact rhGH, $4_1$ (Bag 1), $4_1$ (Bag 2), and $5_1$ (Bag1+2), Table 2, are within limits for an approved biological activity. Values are also of the same magnitude as for the untreated peptide, none compact rhGH (4 and 5 Bag1+2) this suggests that the procedure to compact rhGH does not change the biological activity of rhGH as determine with HI-HPLC-method.

Biological activity of Compact rhGH and None Compact rhGH were evaluated after parental injections in Hypophysis-Ectomised (H-x) rats.

The dose response of 0.04 IU/ml and 0.16 IU/ml of Compact rhGH and of None Compact rhGH were evaluated in groups of 10 H-x rats. A group was treated with a placebo solution*.

* Bovine albumin 12.5 ml (200 mg/ml) was diluted with iso-tonic NaCl to 1000 ml. This solution, Diluent 1.25% Albumin, was used as placebo and to dilute the solutions of Compact rhGH and None Compact rhGH to doses for animal trials.

Solutions from the dialyse—tubes Compact rhGH, 5.3 mg/ml and none compact rhGH 14.2 mg/ml, were aseptically diluted with distilled water and assayed; Compact rhGH, 0.23 mg/ml or 0.69 IU/ml and None Compact rhGH to 0.48 mg/ml or 1.45 IU/ml.

Injection solutions of compact and of none compact rhGH were prepared by dilution with Diluent 1.25% Albumin solution to desired strength, low dose 0.04 IU/ml and high dose 0.16 IU/ml. Diluent 1.25% Albumin solution was used as placebo.

Figure 10:
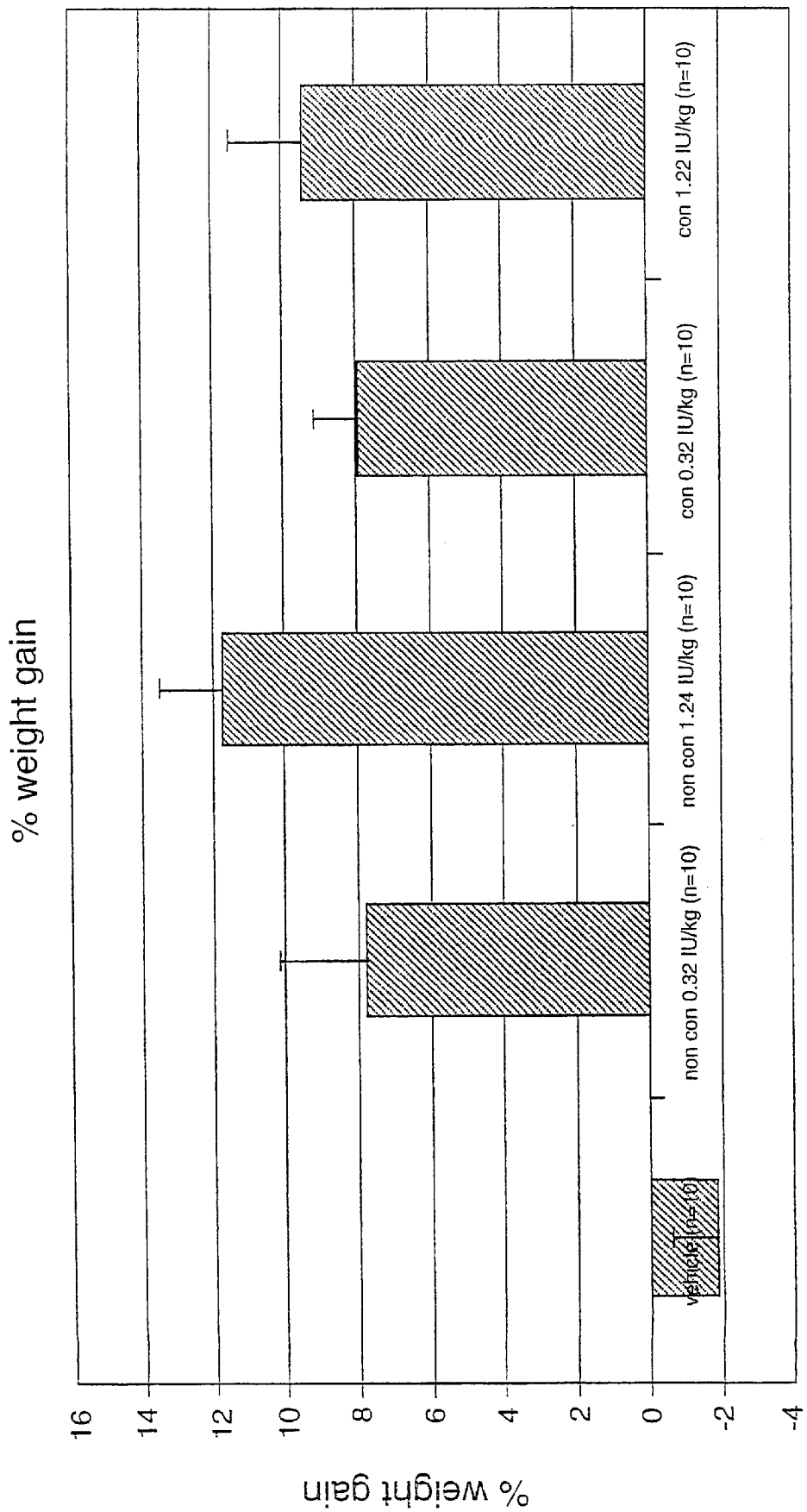
FIG. 10 is illustrating procent weight gained in procent of administrated dose.

FIG. 10 is illustrating procent weight gained in procent of administered dose (treatment of rhGH in i.u./kg body weight for different doses). Dose response of Compact and None Compact rhGH in % weight gain is demonstrated in FIG. 10 of and Table 20 after subcutaneous injection in H-x rats.

TABLE 20

Weight Gain in % given as mean of ten H-x rats. ($X_{n=10 \, in}$ %)

| Preparation | Compact rhGH | | None compact rhGH | | Placebo |
|---|---|---|---|---|---|
| Dose in IU/kg Body-weight | 0.32 | 1.22 | 0.32 | 1.24 | 0 |
| % Weight Gain | 8 | 10 | 8 | 12 | -2 |

Figure 1:
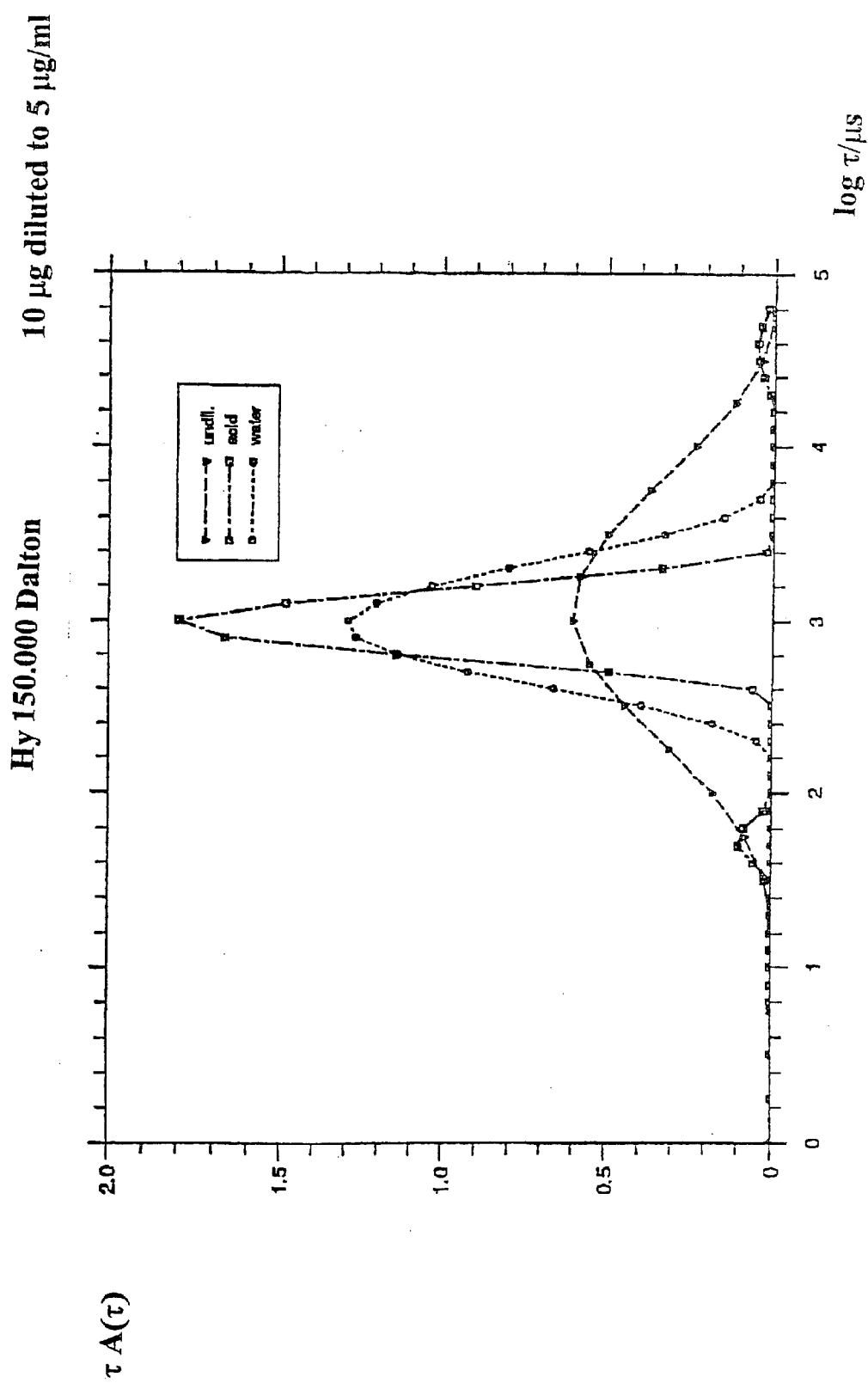
FIG. 1 shows the correlation function distribution for hyaluronic acid at a concentration of 10 μg/ml (with dilutions with water and acid to 5 μg/ml).
Figure 2:
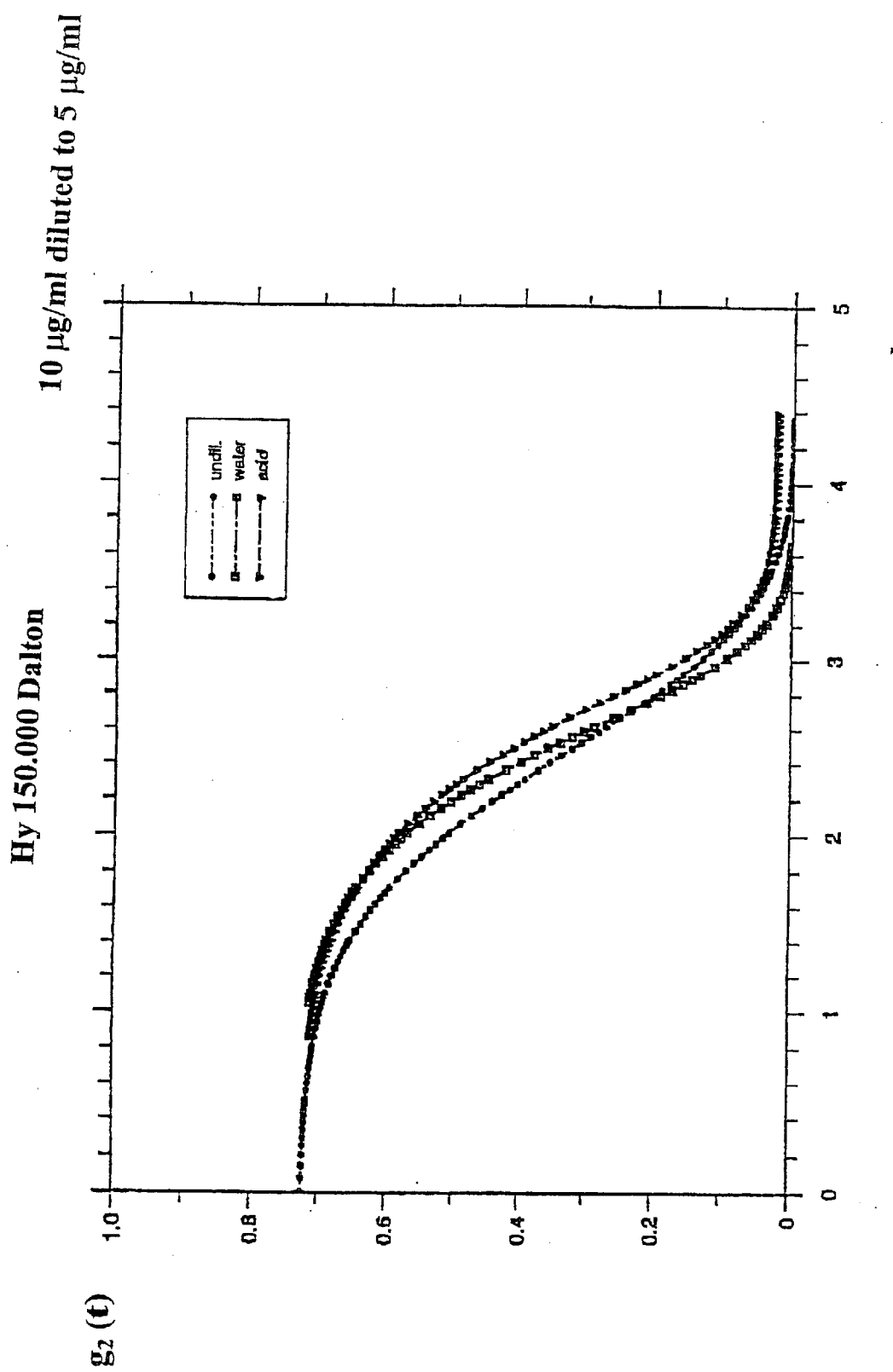
FIG. 2 shows the relaxation time distribution for hyaluronic acid at a concentration of 10 μg/ml (with dilutions with water and acid to 5 μg/ml).
Figure 3:
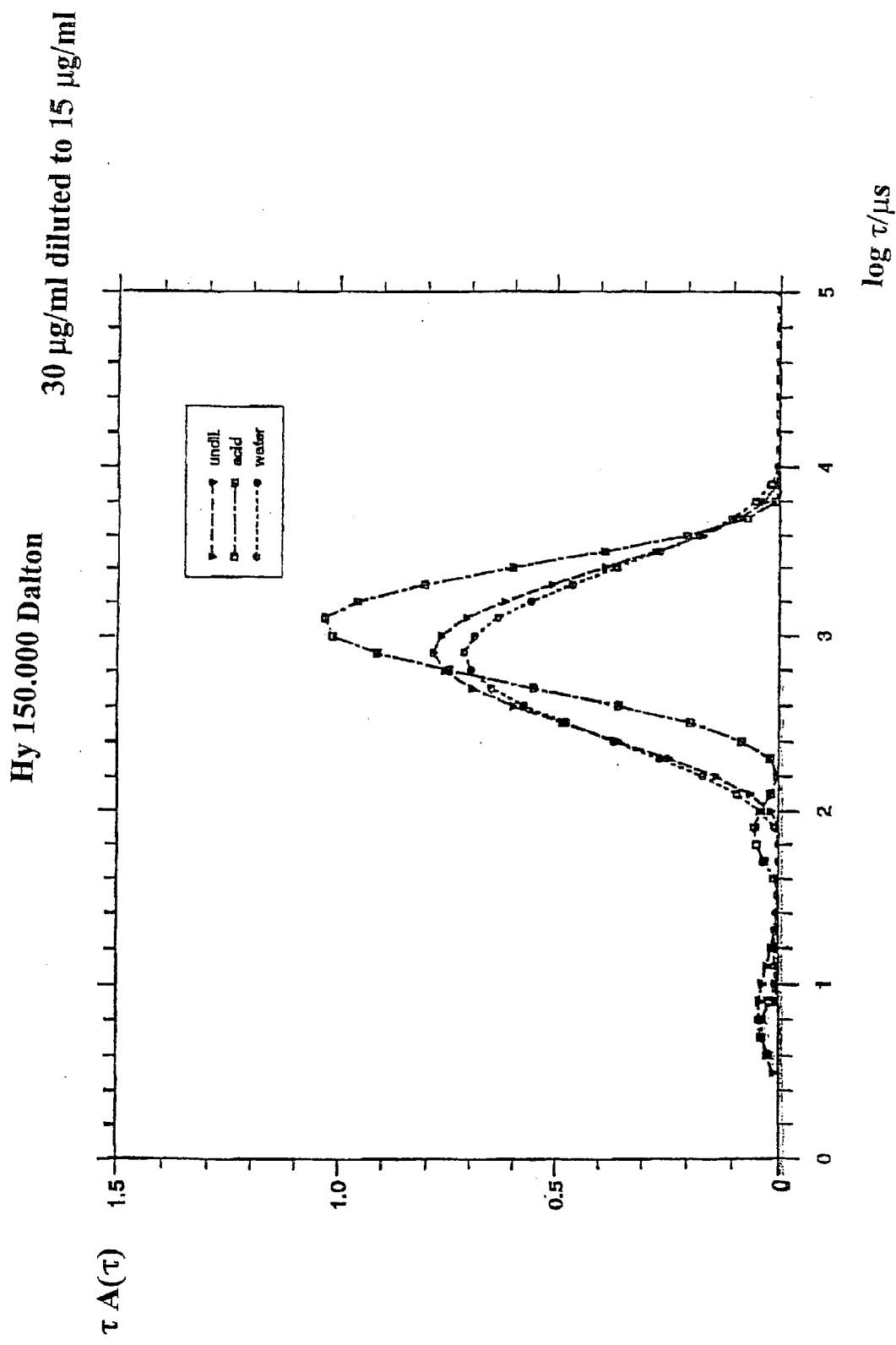
FIG. 3 shows the correlation function distribution for hyaluronic acid at a concentration of 30 μg/ml (with dilutions with water and acid to 15 μg/ml).
Figure 4:
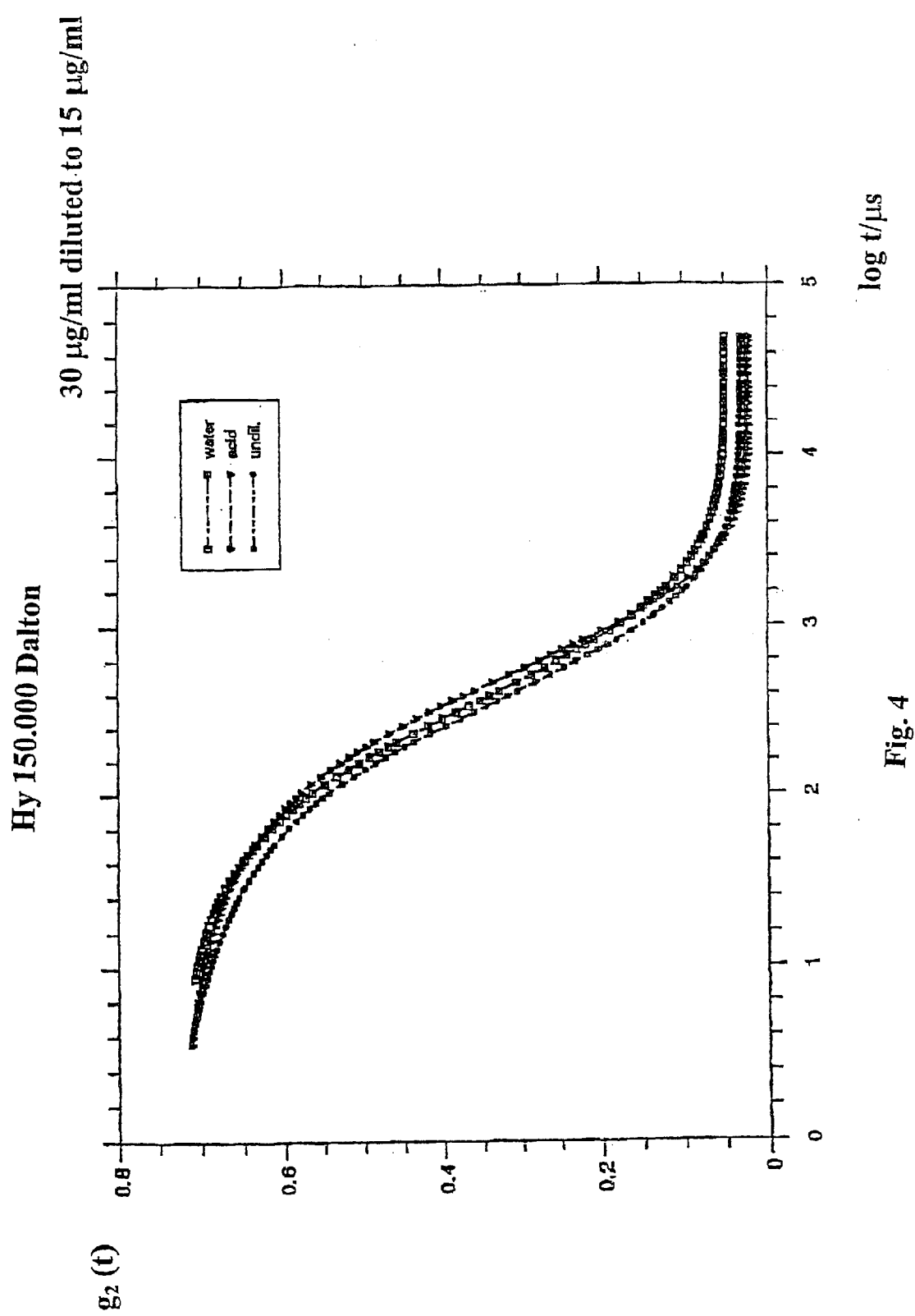
FIG. 4 shows the relaxation time distribution for hyaluronic acid at a concentration of 30 μg/ml (with dilutions with water and acid to 15 μg/ml).
Figure 5:
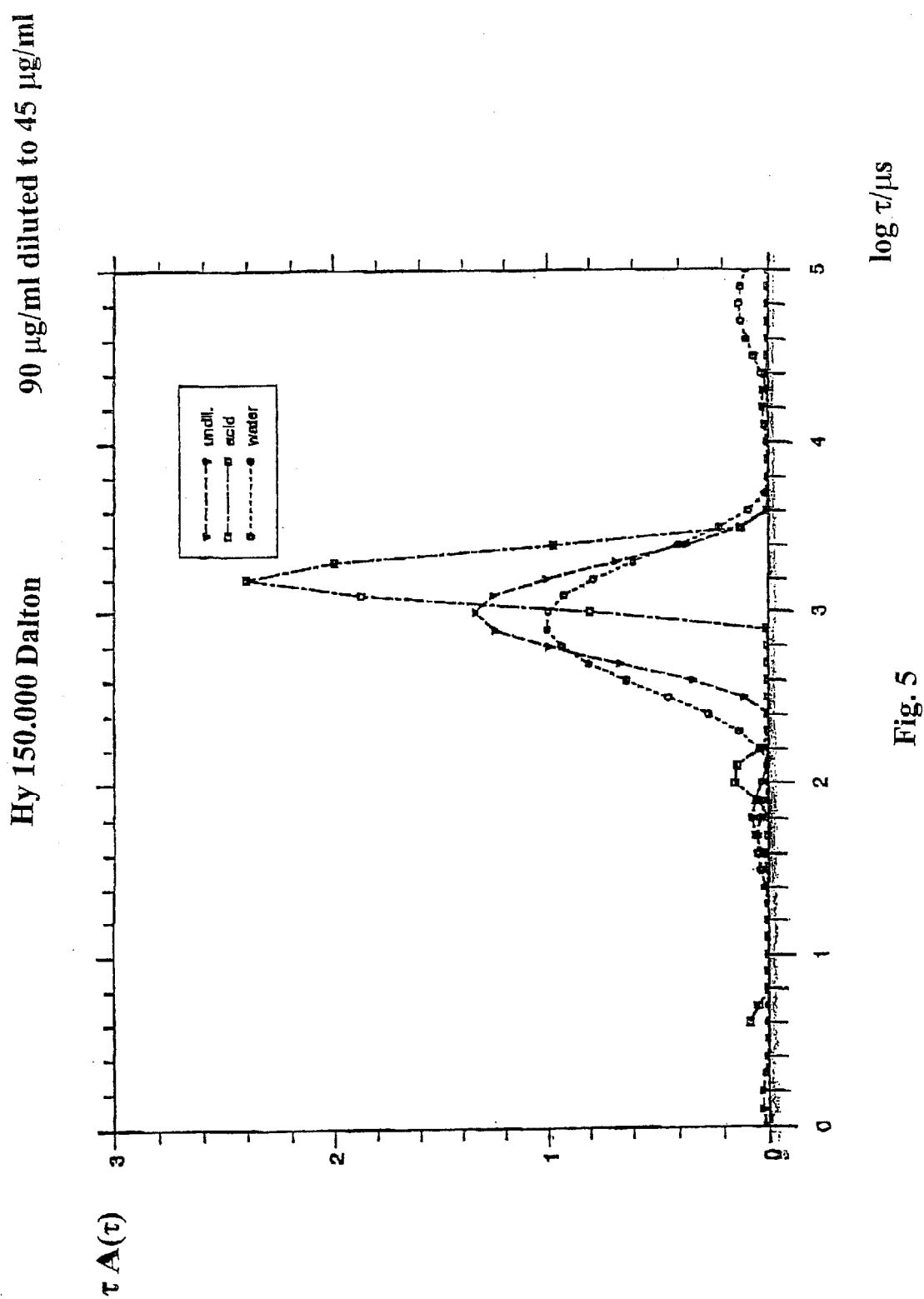
FIG. 5 shows the correlation function distribution for hyaluronic acid at a concentration of 90 μg/ml (with dilutions with water and acid to 45 μg/ml).
Figure 6:
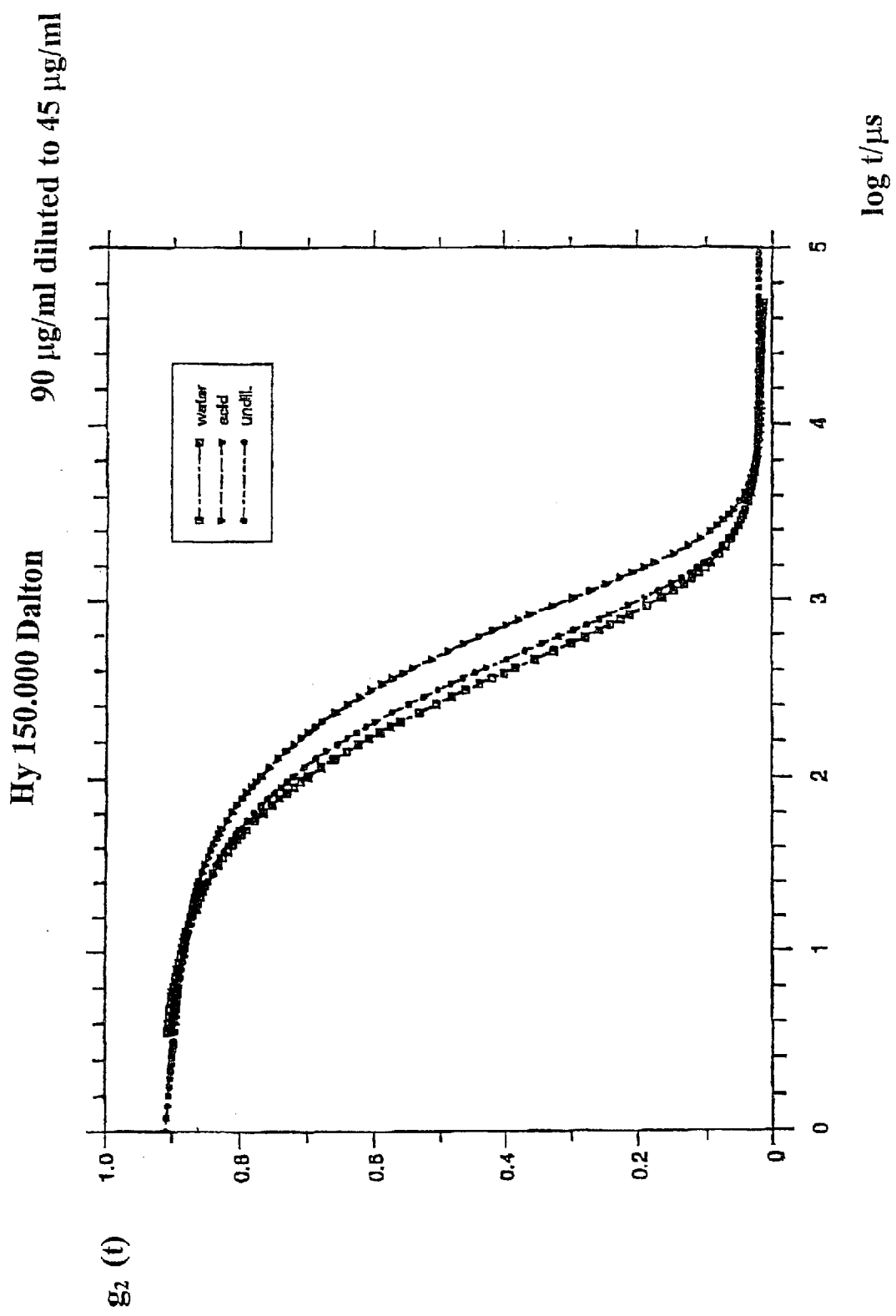
FIG. 6 shows the relaxation time distribution for hyaluronic acid at a concentration of 90 μg/ml (with dilutions with water and acid to 45 μg/ml).

A dose response in % weight gain is demonstrated for Compact and for None Compact rhGH in FIG. 1 and Table 3.

That is for: Compact rhGH 8% weight gain for 0.32 IU/kg and 10% for 1.22 IU/kg.

None Compact rhGH 8% weight gain for 0.32 IU/kg and 12% for 1.24 IU/kg.

For Placebo no weight gain is obtained.

Conclusion: The dose response obtained for Compact rhGH in H-x rats suggests that full biological effect be obtained after the compacting of the rhGH structure.

Particle sizing of Compact and of None Compact rhGH was per-formed with DynaPro-801. The hydrodynamic radius (Rh) is derived from the Transnational Diffusion Coefficient using Stokes-Einstein-.

Equation. The estimated molecular weight is calculated in DynaPro-801 from $R_h$ and the sample temperature using standard curve of MW vs. $R_h$ for globular proteins.

The particle size of Compact and None Compact rhGH was determined at 18, 25 and 30° C. after storage at 5–8° C. for 21 days. Compact rhGH was studied at two different concentrations 1.5 mg/ml and 5.3 mg/ml at 25 and 30° C. None Compact rhGH was studied for one concentration, 14.2 mg/ml, at 18, 25 and 30° C. These were the concentrations obtained from the dialyze bags.

A bimodal function is applied for Compact rhGH and the results present a two-size distribution with its own amplitude, size and MW. For None Compact rhGH the distribution is mono-modal and is fully resolved.

TABLE 21

Particle size of Compact and of None compact rhGH determined with Dynapro-801.
Given radii represents mean of 10 measurements

| | Compact rhGH 1.5 mg/ml | | | | Compact rhGH 5.3 mg/ml | | | | None Compact rhGH 14.2 mg/ml | | |
|---|---|---|---|---|---|---|---|---|---|---|---|
| Temp. °C. | 18 | | 25 | | 25 | | 30 | | 18 | 25 | 30 |
| Type of function | bimodal | | bimodal | | bimodal | | bimodal | | Monomodal | Monomodal | Monomodal |
| % mass | 100 | 0 | 100 | 0 | 98 | 2 | 98 | 2 | 100 | 100 | 100 |
| Est. MW in KDa | 165 | 41281 | 142 | 32115 | 716 | 63666 | 1125 | 83646 | 24 | 24 | 23 |
| Particle size Radii in nm | 5.3 | 51.5 | 4.9 | 46.2 | 9.4 | 61.6 | 11.4 | 68.9 | 2.4 | 2.4 | 2.4 |

Comments to Table 20

The particle size of Compact rhGH was determined at a concentration of 1.5 mg /ml at 18 and 25° C.; 18° C.

100% of the mass contains of a polymer with radii of 5.3 nm and a molar mass of 165 kDa.

The polymer contains of 7.5 rhGH units (molar mass of polymer/molar mass of rhGH; or 165 000/22.124=7.5) with radii of 0.70 nm (radii of polymer/number of rhGH units contained in the polymer; or 5.3/7.5=0.7) 25° C.

100% of the mass contains of a polymer with radii of 4.9 nm and a molar mass of 142 kDa.

The polymer contains of 6.4 rhGH units (142/22.124) with radii of 0.77 nm (4.9/6.4).

The particle size of Compact rhGH was determined at a concentration of 5.3 mg/ml at 25 and 30° C. 25° C.

98% of the mass contains a polymer with radii of 9.4 nm and a molar mass of 716 kDa.

The polymer contains of 32.4 rhGH units (716/22.124) with radii of 0.29 nm (9.4/32.4). 30° C.

98% of the mass contains a polymer with radii of 11.4 nm and a molar mass of 1125 kDa.

The polymer contains 50.8 rhGH units (1125/22.124) with a radii of 0.22 nm (11.4/50.8).

MW rhGH=22124 Da.

TABLE 21

Properties of compacted rhGH

| Compact rhGH structure | | | | |
|---|---|---|---|---|
| Assayed concentration in mg/ml | 1.5 | | 5.3 | |
| Temp. at size measurements ° C. | 18 | 25 | 25 | 30 |
| Molar mass of the polymers in kDa | 165 | 142 | 716 | 1125 |
| Hydrodynamic radii of the polymers in nm | 5.3 | 4.9 | 9.4 | 11.4 |
| Number of compacted units rhGH in the polymers | 7 | 6 | 32 | 50 |
| Estimated hydrodynamic radii of one compacted rhGH-unit in the polymer in nm | 0.70 | 0.77 | 0.22 | 0.29 |

Conclusion: The radii of Compact rhGH are smaller than None Compact rhGH. That is, at a concentration of 5.3 mg/ml one compacted unit of rhGH is estimated to have hydrodynamic radii of 0.22–0.29 nm and at 1.5 mg/ml 0.70–0.77 nm. At a concentration of 14.5 mg/ml None Compact rhGH is estimated to have a hydrodynamic radii of 2.4 nm. The number of units of compacted rhGH contained in a polymer is found to depend on the concentration of the solution. Upon dilution no agglomerate of the polymers were found.

Conclusion of example 5: By changing pH to a strong acid solution (pH 1.5) rhGH gets easily soluble and Hy becomes a charged structure stretching out from a curling cylinder to straight line. By adding electrolytes to the solution a minimum of charge occurs in the peptide. This results in a total collapse of the peptide structure as it passes its pI (isoelectricpoint). In regulating the ions (NaCl and $Na_2SO_4$) and the rhGH concentrations with the speed of the pH-change when passing the pI. the hydrodynamic radii of the particles in the dispersion of the peptide are changed from 2.4 to 0.22 nm. Hy stabilize the dispersion in changing its structure back to a curling like structure when pH is changed to pH 6. It is then possible to dilute the dispersions to the concentration desired. The hydrophobic properties of the rhGH structure is found to be optimal as pH is changed in a strong acid solution pH<2 and by dialyses transferred to neutral solution pH 6 as demonstrated in Example 5.

What is claimed is:

1. A method for manufacture of a hydrophobic biomolecular structure consisting of hyaluronic acid and a polar substance, said hyaluronic acid surrounding the polar substance and said polar substance having a reduced size, wherein the method comprises:
   solubilization of the hyaluronic acid in an aqueous solution of an electrolyte and an acid, to form a mixture of solubilized hyaluronic acid, an electrolyte and an acid;
   solubilization of the polar substance in said mixture;
   adjusting the pH of said mixture including the solubilized polar substance to a pH below pH 3 thereby to expose hydrophobic domains of the polar substance; and
   dialyzing said mixture so as to reduce an ionic concentration thereof past the point of collapse for said polar substance, thereby to form a collapsed polar structure wherein said hyaluronic acid surrounds said polar substance;
   wherein said hyaluronic acid exposes at least part of its hydrophobic domains and surrounds, binds and stabilizes the polar substance by hydrophobic interactions, to form said hydrophobic biomolecular structure.

2. The method according to claim 1, wherein the acid for solubilization of the hyaluronic acid and the solubilization of the polar substance is selected from the group consisting of hydrochloric acid, phosphoric acid and acetic acid.

3. The method according to claim 1, wherein said electrolyte is selected from the group consisting of $NH_4^+$, $K^+$, $Na^+$, $Ca^{2+}$, $Zn^{2+}$, $Fe^{2+}$, $Fe^{3+}$, sulphates, chlorides, and acetates.

4. The method according to claim 1, wherein the pH during the dialysis of the mixture of the solubilized hyaluronic acid and the solubilized polar structure is in the range of 1.5 to 7.5, the dialysis ending at a final pH in the range of 5.5 to 7.5.

5. The method according to claim 1, wherein said hyaluronic acid has a molecular weight les than 400 kDa.

6. The method according to claim 1, wherein said adjusting step comprises adjusting the pH of said mixture to a pH of 1.0 to 3.0.

7. The method according to claim 1, wherein said adjusting step comprises adjusting the pH of said mixture to a pH of 1.0 to about 1.5.

* * * * *